(12) United States Patent
Kelman

(10) Patent No.: US 6,419,697 B1
(45) Date of Patent: Jul. 16, 2002

(54) CLIP-ON OPTIC ASSEMBLY

(76) Inventor: Charles David Kelman, 721 Fifth Ave., New York, NY (US) 10022

( * ) Notice: Subject to any disclaimer, the term of this patent is extended or adjusted under 35 U.S.C. 154(b) by 21 days.

(21) Appl. No.: 09/612,181

(22) Filed: Jul. 7, 2000

(51) Int. Cl.[7] .................................................. A61F 2/16
(52) U.S. Cl. ..................................... 623/6.43; 623/6.33
(58) Field of Search ....................... 623/6.34, 6.11–6.38, 623/6.32, 6.33

(56) References Cited

U.S. PATENT DOCUMENTS

| | | |
|---|---|---|
| 4,932,971 A | 6/1990 | Kelman |
| 5,366,502 A * | 11/1994 | Patel .............................. 623/6 |
| 6,267,784 B1 * | 7/2001 | Benz et al. ................. 623/6.59 |

* cited by examiner

Primary Examiner—Corrine McDermott
Assistant Examiner—Thomas Barrett
(74) Attorney, Agent, or Firm—Darby & Darby

(57) ABSTRACT

A supplemental lens assembly for attachment to the position fixation means of a primary intraocular lens to change its optical characteristics. The assembly comprises a supplemental lens body with at least one connecting member extending from it and adapted for attachment to the position fixation means of the primary lens.

21 Claims, 3 Drawing Sheets

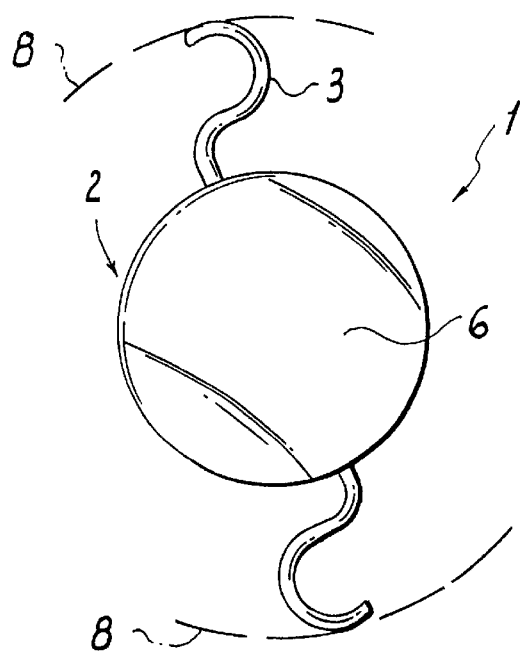
Fig. 1
(Prior Art)
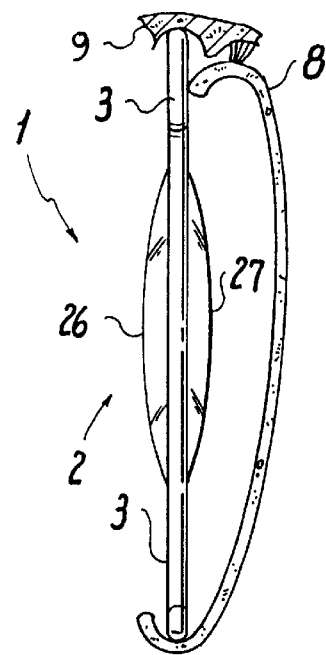
Fig. 2
(Prior Art)
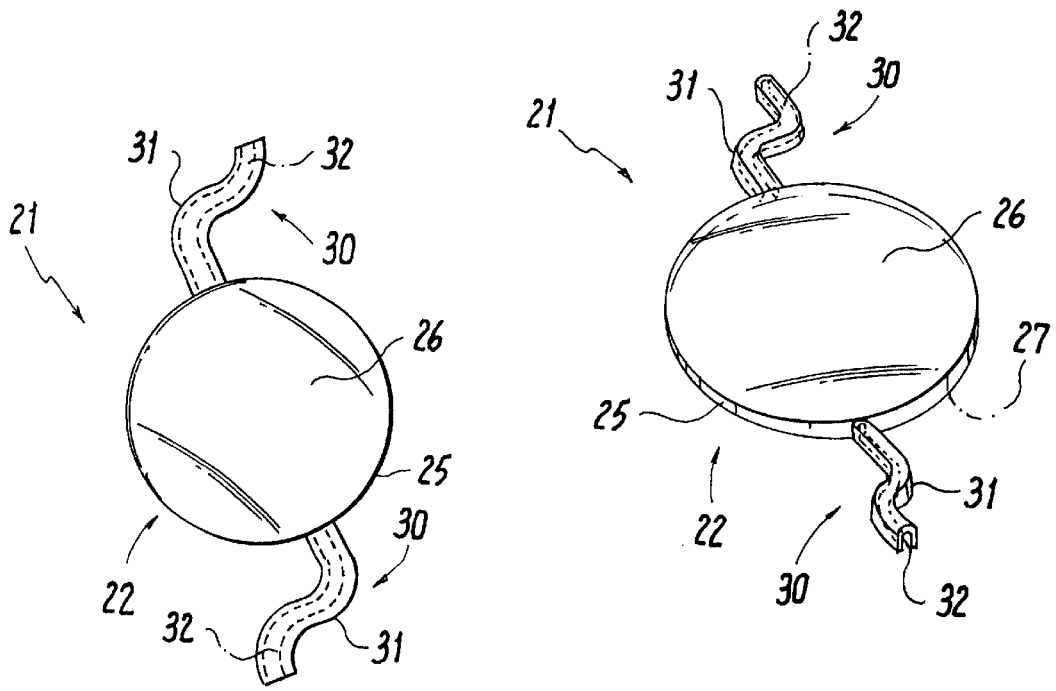
Fig. 3
Fig. 4

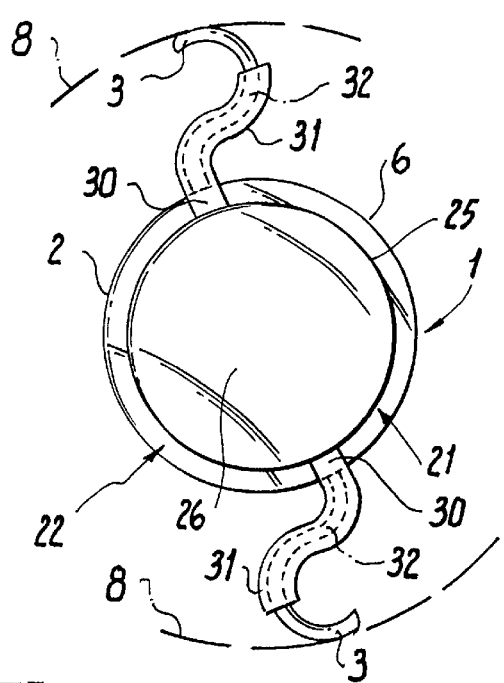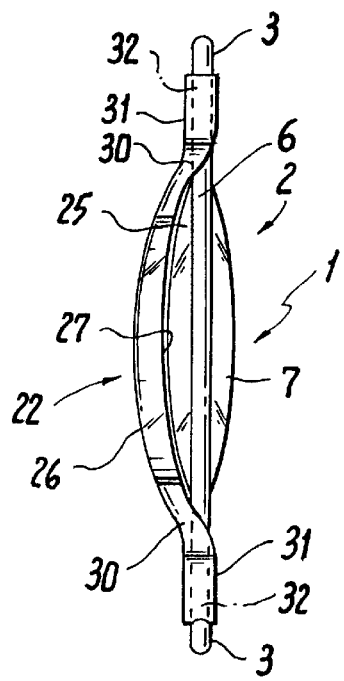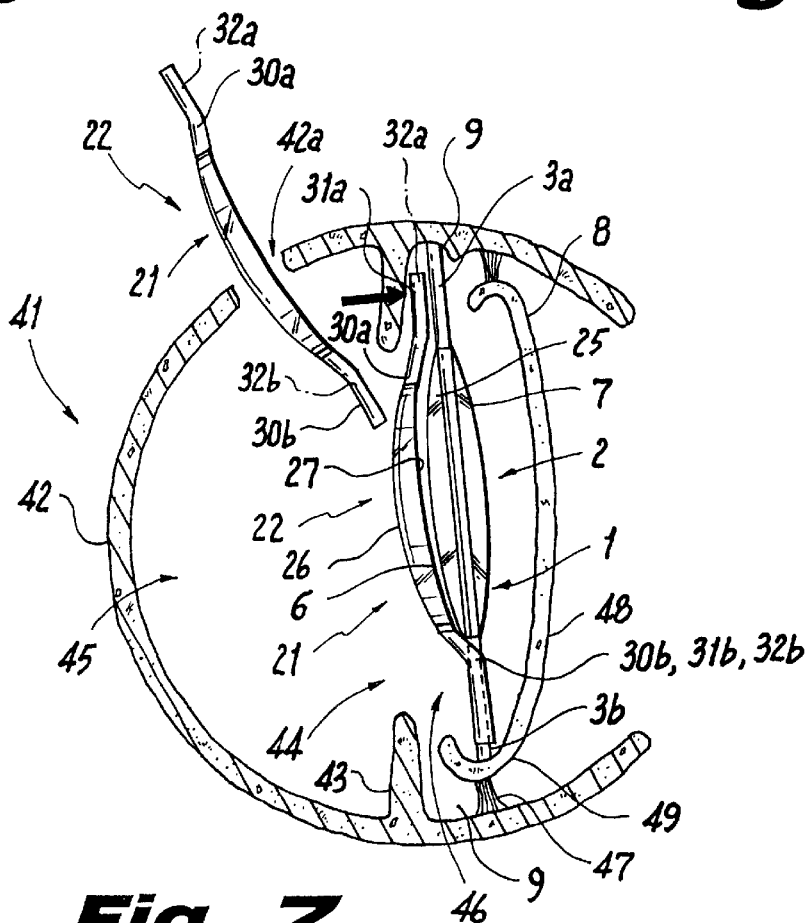

CLIP-ON OPTIC ASSEMBLY

BACKGROUND OF THE INVENTION

1. Field of the Invention

The present invention relates to a clip-on optic assembly, or, supplementary IOL, and more particularly to such an assembly that is capable of being clipped in-situ onto a previously implanted artificial intraocular lens to change the optical characteristics thereof without having to remove the implanted lens from the eye.

2. Description of Related Art

Intraocular lenses have long been used in patients whose vision has deteriorated due to a variety of conditions, including cataracts, myopia, and other diseases. In some instances, the natural lens is removed and an intraocular lens is implanted to provide the light-focusing optic for the eye. In other instances, the natural lens is not removed and the intraocular lens is implanted against the natural lens, cooperating with it to enhance deteriorated vision.

For various reasons, the implanted intraocular lens is not always sufficient to permanently provide desired vision characteristics. The patient's condition may change over time or as a degenerative disease progresses. It may not have been technologically feasible to manufacture a lens with the desired optical characteristics at the time of implantation. The implanted lens may even contain an undiscovered optical defect that prevents proper focusing of images on the retina, or a lens of improper power may have been erroneously implanted. Thus, it is desirable and frequently necessary to correct the resulting vision deficiency.

While removal and replacement of the implanted lens is usually possible, it is often not practical or desirable. Due to tissue growth around the haptics or other position fixation means used to maintain the already implanted lens in the eye, as well as adhesion of eye tissue to other portions of the implant, especially when the lens has been implanted for an extended period of time, its removal and replacement involves complex surgery and the risk of loss of vision. Regardless, the minimizing of surgical intrusion is always preferable as it represents lower risk to the patient.

To this end, optic assemblies capable of being placed insitu in the eye onto a previously implanted intraocular lens have been developed. U.S. Pat. No. 4,932,971, issued Jun. 12, 1990 to Kelman shows an optic assembly capable of being clipped onto a previously implanted intraocular lens. The assembly is inserted through an incision into the eye, and clip members attached to the lens body of the assembly are manipulated so that they extend over the peripheral edge of the optic of the previously implanted lens, gripping the assembly thereto. The optic assembly may be manufactured with an optical profile that selectively corrects deficiencies of the original implanted lens or provides selected desired vision characteristics.

In the Kelman '971 optic assembly, the clip members extend over portions of the surface of the first, already implanted intraocular lens. This has the effect of the clip members interfering with light passing through the first lens, and may thereby interfere with the final visual image formed on the retina.

Thus, it would be desirable to provide a clip-on optic assembly to furnish patients already having an implanted intraocular lens with improved visual acumen without subjecting them to the risk associated with complex surgery in removing the implanted lens and replacing it with a new one, while minimizing interference of light passing through the implanted lens due to clip members extending over portions of it.

SUMMARY OF THE INVENTION

It is an object of the present invention to provide a clip-on optic assembly.

It is another object of the invention to provide a clip-on optic assembly capable of being clipped in-situ onto a previously implanted artificial intraocular lens to change the optical characteristics thereof without removing such implanted lens from the eye.

It is another object of this invention to provide a clip-on optic assembly that minimizes interference, by the clip members, with light passing through an implanted, or primary, intraocular lens when clipped thereon.

It is a further object of this invention to provide a clip-on optic assembly of a construction enabling an associated minimum risk method for insertion of the assembly through an incision into the eye.

The present invention is a clip-on optic assembly. The assembly is capable of being clipped in-situ onto a previously implanted, or primary intraocular lens to change its optical characteristics without having to remove the implanted or primary lens from the eye or having to seat additional haptics in the eye tissue, while minimizing interference by the assembly of light passing through the primary lens.

The optic assembly comprises a supplementary lens body and at least one clip member extending from the supplementary lens body. The clip member has a grip forming a cavity capable of receiving and gripping at least a portion of a haptic or other position fixation means of the primary implanted lens. Desirably, the clip member or members are sufficiently resilient to permit temporary flexing to facilitate insertion of the supplementary assembly through a minimum size incision into the eye.

The lens body of the supplementary lens preferably has a peripheral size corresponding substantially to the peripheral size of the optic of the primary intraocular lens and a posterior surface shaped to substantially correspond to the anterior surface of the optic of the primary intraocular lens for mounting the supplementary lens thereon. The supplementary lens cooperates with the primary intraocular lens for selectively modifying the optical characteristics of the primary intraocular lens. The supplementary lens may have multi-focal characteristics for providing a multi-focal vision system when clipped onto the primary intraocular lens. The supplementary lens may also be shaped to correct an optical defect of an implanted primary lens discovered after implantation or an improper power of an erroneously installed lens.

This invention contemplates a combination of a supplementary optic assembly clipped onto an implanted primary intraocular lens, which includes in-situ attachment of the optic assembly onto a previously implanted intraocular lens. The invention also contemplates a corresponding method of providing the combination by attachment of the supplementary lens assembly to an primary intraocular lens before inserting the combined optic assembly through an incision into the interior of an eye. The attachment is effected by situating the posterior surface of the supplementary lens body against the anterior surface of the primary intraocular lens and then manipulating, e.g., clamping, the clip member onto a haptic or other position fixation means of the primary intraocular lens.

Other objects and advantages of the present invention will become apparent from the specification and accompanying drawings.

BRIEF DESCRIPTION OF THE DRAWINGS

FIGS. 1 and 2 show a schematic front view and side view, respectively, of a prior art previously implanted primary intraocular lens having a pair of diametrically opposed haptics in engagement with the adjacent tissue in the eye.

FIGS. 3 and 4 show a schematic front view and an oblique view, respectively, of a supplemental optic assembly according to an embodiment of the present invention.

FIGS. 5 and 6 show schematic front and side views respectively, of a combination of the supplemental optic assembly of FIGS. 3 and 4 clipped onto the primary implanted lens of FIGS. 1 and 2 according to the present invention.

FIG. 7 shows a schematic sectional view of an eye showing the method of inserting the supplemental optic assembly of FIGS. 3 and 4 via an incision for clip-on mounting in situ on the implanted primary lens of FIGS. 1 and 2 to form the combination of FIGS. 5 and 6 according to the present invention.

DESCRIPTION OF THE PREFERRED EMBODIMENTS

Figure 8:
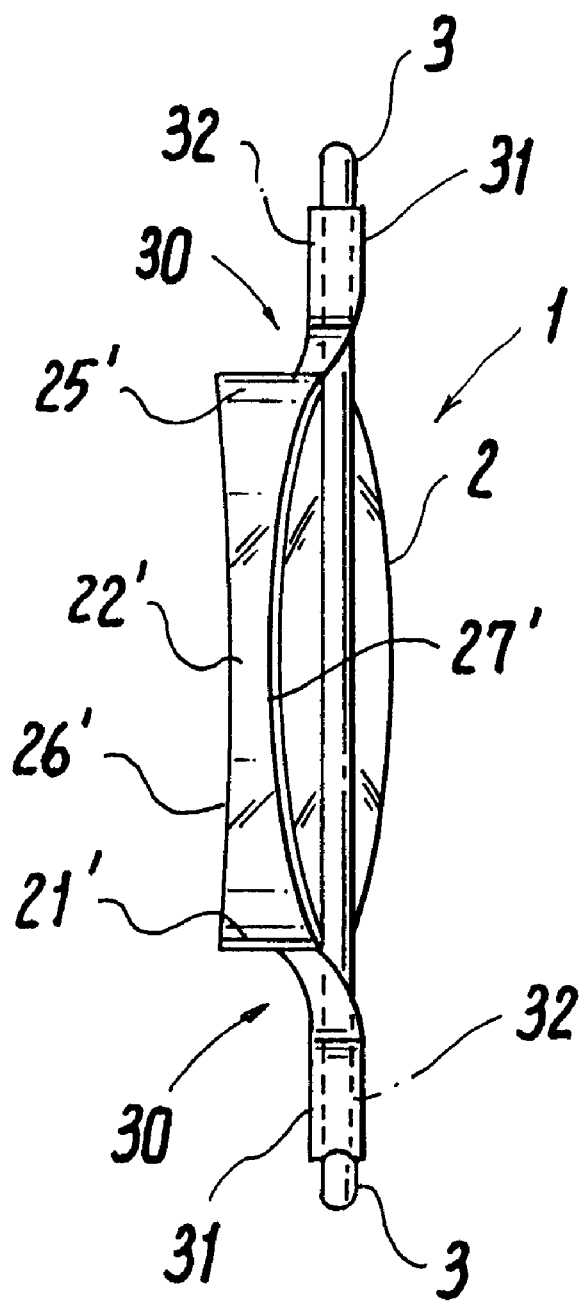
FIG. 8 shows a schematic side view of an supplemental optic assembly having a concave-concave optic mounted on an primary intraocular lens according to an embodiment of the present invention.

Referring to the drawings, and initially to FIGS. 1 and 2, a prior art previously implanted artificial intraocular lens 1 is shown, including an optic 2 having position fixation means such as a pair of opposed haptics 3 outwardly extending therefrom, e.g., generally radially, and seated against adjacent eye tissue 8, 9 (shown in phantom) to implant lens 1 in the eye in the usual manner. The optic 2 has anterior and posterior surfaces 6, 7, respectively, which, for instance, may be of generally convex shape.

As shown in FIGS. 3 and 4, according to one embodiment of the present invention, a supplemental clip-on assembly 21 is provided having a lens body 22 with a peripheral size similar to that of the optic 2, such as about 5–6 mm in diameter as compared to about 6 mm diameter for the optic 2, and at least one and preferably two clip members 30 extending, preferably, generally radially, from the lens body 22. Each clip member 30 has a grip 31 forming a cavity 32. In another embodiment, the lens body 22 has a diameter of about 3–5 mm.

The lens body 22 of the supplemental assembly 21 preferably also has a circular peripheral edge 25 and anterior and posterior surfaces 26, 27, respectively. While the anterior surface 26 is of generally convex shape, the posterior surface 27 is of generally concave shape and is specifically configured to generally counterpart the shape of the anterior surface 6 of the optic 2. Regardless, the lens body 22 is provided with an overall shape and size specifically adapted to change the existing optical characteristics of the optic 2 in the desired manner when clipped thereto, as shown in FIGS. 5 and 6.

To achieve clipping of the assembly 21 onto an intraocular lens 1 the assembly 21 is selectively configurable so that the cavity 32 of the grip 31 may receive and grip a haptic 3. The clip member 30 is attached to the lens body 22 at a selective location, and has a shape and length such that the resilient walls of the cavity 32 can grip at least a portion of the haptic 3. Preferably, the grip 31 is in the form of a split sleeve such that the walls of the cavity extend at least partially around a haptic 3 and the resilient nature of the grip 31 grips it to the haptic 3 of the lens 1. In a preferred embodiment, the cavity 32 formed by the split sleeve has a shape roughly conforming to the exterior surface of the haptic 3 in the region where the sleeve 32 grips the haptic 3. In the preferred embodiment, the number of clip members 30 are equal to the number of haptics 3, or other position fixation means, to provide sufficient gripping of the haptics 3 while minimizing the size of the clip members 30. Although the above embodiments show two clip members and two haptics, it will be understood that any number of clip members may be provided as desired.

As shown in FIG. 7, the eyeball 41 includes the cornea 42 and the iris 43, the latter forming the adjustable central pupil opening 44 that separates the anterior chamber 45 from the posterior chamber 46. An previously implanted primary lens 1 is typically positioned in the posterior chamber 46 after extracapsular removal of the natural eye lens (not shown) by known surgical procedures, with both haptics seated in the capsular bag 8, with one haptic seated in the capsule 8 and the other haptic in the ciliary sulcus 9, or both haptics seated in the capsule, or both haptics seated in the ciliary sulcus.

For combining the assembly 21 with an already implanted intraocular lens 1 to produce desired optical characteristics of the combination, the supplemental lens assembly 21 is preferably inserted through a minimum size incision 42a (FIG. 7). Generally, the incision 42a would be of size or length just sufficient for the lens body 22 to pass therethrough.

Once the supplemental lens assembly 21 is inserted in the eye, the posterior surface 27 of the lens body 22 is positioned on the anterior surface 6 of the primary optic 2. The clip member 30 is then clipped onto a haptic 3 by pressing or manipulating the grip member 31 onto the haptic 3 such that the cavity 32 receives and grips at least a portion of the haptic 3. In FIG. 7, the clip member 30b is shown in a clipped-on position such that the cavity 32b of the grip 31 has received the haptic 3b, while the clip member 30a is shown in an unclipped position. In one embodiment, where the grip 31a is sufficiently resilient, it temporarily flexes to fit around the haptic 3a as the grip 31a is pressed onto it such that the walls of cavity 32a grip the haptic 3a. It will be understood by one skilled in the art, however, that there are other means for gripping a haptic 3, other than "pressing on."

One skilled in the art will also recognize that the supplemental assembly 21 may be clipped onto an primary intraocular lens 1 outside of the eye, e.g., before the intraocular lens 1 is implanted.

As mentioned above, a lens body 22 may be provided with an overall shape and size specifically adapted to change the existing optical characteristics of an optic 2 in the desired manner when clipped thereon. As shown in FIGS. 5 and 6, the lens body 22 or, supplementary IOL, has a peripheral size close to the peripheral size of the optic 2, e.g., about 5 mm diameter for an optic of about 5 mm diameter, and a concave posterior surface 27 in substantially conforming surface contact with the anterior surface 6 of the optic 2 of the primary intraocular lens 1. Substantially conforming surface contact includes having the overlying surfaces separated from one another by a thin layer of fluid.

As the optical characteristics of an implanted optic 2 are already known, a lens body 22 can be fabricated to provide it with optical characteristics designed to compensate for an existing defect. For example, the resulting combination of the optic 2 and the lens body 22 will correct an improper power of the optic 2, obviating the defect.

In a preferred embodiment, the lens body 22 is manufactured with multi-focal, i.e., at least bifocal, characteristics to provide a resultant multi-focal system when combined with an intraocular lens 1. In such an embodiment, each region of the lens body 22, having different focal characteristics relative to the optic 2 of the intraocular lens 1, serves as an optical add-on in combination with the optic 2. For instance, the lens body 22 of FIGS. 5 and 6 may have a central portion relative to the optic 2 that serves as a bifocal add-on, e.g., has a high "plus" diopter, such that the central region of the lens body 22 and the underlying central portion of the optic 2 provide for near, or close, reading vision, while the peripheral portions of the lens body 22 and the underlying peripheral portion of the optic 2 provide for far, or distant, vision.

Those skilled in the art will recognize that according to the present invention, depending on the optical and other characteristics sought, the lens body 22 of the supplemental lens may be of any suitable shape, size and focal or multi-focal characteristics for use with an intraocular lens 1. FIG. 8 shows an embodiment in which the assembly lens body 22' has a concave anterior surface 26', a concave posterior surface 27', and a wide peripheral side wall 25'.

Those skilled in the art will understand that a previously implanted intraocular lens need not be located in the posterior chamber 46 as shown in FIG. 7, but instead may be located in the anterior chamber 45 or in a different disposition in the posterior chamber 46 than that shown in FIG. 7, and that the supplemental assembly 21 may be clipped in-situ thereon in an equally facilitated manner to change the optical characteristics of such a previously implanted intraocular lens 1.

Thus, compared to the procedure heretofore for replacing a previously implanted primary intraocular lens in patients suffering from vision impairment, which may subject a patient to the risks of complex surgery, including loss of vision, or alternatively, installing an optic assembly onto an implanted primary intraocular lens that has attachment members that may interfere with light passing through the primary lens, the present invention achieves the desired result of mitigating visual impairment while minimizing the interference of light passing through the previously implanted primary intraocular lens and also eliminating the need for the complex surgery involved in removing the previously implanted intraocular lens.

All materials used in making an supplemental lens assembly 21 will be compatible with the internal eye environment and thus non-toxic. The lens body 22 may, by way of example, be made of suitable resilient material such as resilient plastic material, e.g., polymethylmethacrylate (PMMA) or PROLENE (a polypropylene material), or of suitable rigid material such as glass. In any event, the lens body 22 will be formed using known means in appropriate shape and size of suitable light-focusing material having the desired optical characteristics.

Of course, the actual convex or concave shape and corresponding plus or minus diopter value characteristics assigned to a given supplemental lens body 22 will depend upon the optical characteristics of the primary intraocular lens 1 and the nature of the modification thereof intended to be produced by combining the clip-on assembly therewith according to the invention. These factors are well known to the attending ophthalmologist.

However, for optimum efficiency of the combination optical system of an supplementary lens assembly 21 clipped onto an primary intraocular lens 1, the posterior surface 27 of the lens body 22 is shaped to conform substantially to the counterpart shape of the anterior surface 6 of the optic 2 to provide an effective, substantially continuous, generally smooth and even, coextensive surface to surface abutting contact interface relation therebetween, preferably essentially without the existence of any intervening void space, but allowing for a thin film of liquid therebetween. This coextensive conforming contact interface relation between the posterior surface 27 of the lens body 22 and the anterior surface of the optic 2 of the intraocular lens 1 will be taken into account in fashioning the shape and profile of the lens body 22.

The grip 31 may be made of suitable resilient material such as resilient plastic material, e.g., PMMA or PROLENE, preferably formed as a "springy" pliable member having suitable properties, such as shape "memory," to achieve both the aforesaid flexing of the grip 31 and the stated gripping of the haptic 3 or other position fixation means.

Those skilled in the art will appreciate that the foregoing specification and accompanying drawings are set forth by way of illustration and not limitation of the present invention. It will further be appreciated that various modifications and changes may be made therein without departing from the spirit and scope of the present invention, which is to be limited solely by the scope of the appended claims.

What is claimed is:

1. A supplemental lens assembly, capable of being clipped onto a primary intraocular lens, said primary intraocular lens having an optic and at least one position fixation member for seating the primary lens in an eye, said at least one position fixation member extending from said optic, said supplemental lens assembly comprising:

a. a lens body; and
 b. at least one connecting member extending from said lens body beyond a peripheral edge of said lens body, said at least one connecting member being adapted to connect to said at least one position fixation member for attaching the supplemental lens assembly to the primary intraocular lens with said lens body of the supplemental lens assembly overlying the optic of the primary intraocular lens, wherein said at least one connecting member is sufficiently resilient to permit temporary flexing for insertion of the supplemental lens assembly into the eye, wherein said at least one connecting member has the form of a split sleeve for engaging said position fixation member such that said sleeve surrounds at least a portion of said position fixation member.

2. Supplemental lens assembly of claim 1, wherein said lens body has a posterior surface shaped to correspond substantially to an anterior surface of the optic of the primary intraocular lens in a region where said lens body and said optic overlap for seating said lens body on said anterior surface.

3. Supplemental lens assembly of claim 2, wherein said lens body has a peripheral size corresponding substantially to a peripheral size of the optic of the primary intraocular lens.

4. Supplemental lens assembly of claim 3, wherein said lens body has a diameter of about 3–5 mm.

5. Supplemental lens assembly of claim 2, wherein said lens body is shaped for modifying the optical characteristics of the intraocular lens.

6. Supplemental lens assembly of claim 1, wherein said lens body is shaped to provide it with multi-focal optical characteristics.

7. Supplemental lens assembly of claim 1, wherein said sleeve has a shape generally conforming to the shape of the exterior surface of the position fixation member in a region where said sleeve grips the position fixation member.

8. Supplemental lens assembly of claim 1, wherein said at least one connecting member comprises a number of connecting members equal to the number of position fixation members.

9. Supplemental lens assembly of claim 1, wherein said primary intraocular lens has been implanted in an eye, said supplemental assembly being capable of being clipped in-situ onto said primary intraocular lens.

10. An optic combination comprising:
   a. an intraocular lens adapted to be implanted into an interior of an eye, said intraocular lens having an optic and at least position fixation member for seating said intraocular lens in the surrounding tissue of said eye when implanted therein; and
   b. an optic assembly adapted to be clipped onto said at least one position fixation member, said optic assembly having a lens body and at least one connecting member extending therefrom beyond a peripheral edge of the lens body, said connecting member being an elongated resilient member defining a channel, extending along a length of said connecting member, capable of receiving at least a portion of said at least one position fixation member and gripping thereon.

11. Combination of claim 10, wherein said lens body has a peripheral size corresponding substantially to the peripheral size of said optic of said intraocular lens and a posterior surface shaped to correspond substantially to the anterior surface of said optic of said intraocular lens for seating said assembly thereon while modifying optical characteristics of said intraocular lens.

12. Combination of claim 10, wherein said lens body is shaped to provide it with optical characteristics for producing a resultant multi-focal optical system when mounted on said intraocular lens.

13. A method of providing said combination of claim 10, said method comprising clipping said assembly onto said intraocular lens by situating the posterior surface of said lens body against the anterior surface of said optic of said intraocular lens, and then pressing said at least one connecting member onto said at least one fixation member whereby said channel receives said fixation member and grips thereon.

14. Method of claim 13, wherein said lens body has a peripheral size corresponding substantially to the peripheral size of said optic of said intraocular lens and said posterior surface is shaped to correspond substantially to said anterior surface of said optic for seating thereon for modifying optical characteristics of said intraocular lens.

15. Method of claim 13, wherein said lens body is shaped to provide it with optical characteristics for producing a resultant multi-focal optical system when mounted on said intraocular lens.

16. Method of claim 15, wherein said lens body has a peripheral size corresponding substantially to the peripheral size of said optic of said intraocular lens and said posterior surface is shaped to correspond substantially to said anterior surface of said optic for seating thereon for modifying optical characteristics of said intraocular lens.

17. Method of claim 15, wherein said lens body is shaped to provide it with optical characteristics for producing a resultant multi-focal optical system when mounted on said intraocular lens.

18. Method of claim 13, wherein said intraocular lens has been previously implanted into said interior of said eye, further including the step of first inserting said optic assembly through an incision into said eye for in-situ clipping of said assembly onto said previously implanted intraocular lens.

19. A supplemental lens assembly, capable of being clipped onto a primary intraocular lens, said primary intraocular lens having an optic and at least one position fixation member for seating the primary intraocular lens in an eye, said at least one position fixation member extending from said optic, said supplemental lens assembly comprising:
   a. a lens body; and
   b. at least one connecting member extending outwardly from a peripheral edge of said lens body, said at least one connecting member being an elongated resilient member that is shaped so as to connect to said at least one position fixation member for attaching said supplemental lens assembly to said primary intraocular lens with said lens body of said supplemental lens assembly overlying said optic of said primary intraocular lens, wherein said at least one connecting member comprises a U-shaped sleeve having a channel defined therein for receiving the at least one position fixation member.

20. Supplemental lens assembly of claim 19, wherein said at least one connecting member is flexible and has at least one curved portion, said at least one connecting member assuming a shape of at least a portion of said at least one position fixation member to which said at least one connecting member is affixed.

21. Supplemental lens assembly of claim 19, wherein said at least one connecting member extends radially from said peripheral edge of said lens body.

\* \* \* \* \*